(12) United States Patent
Yu

(10) Patent No.: US 8,163,684 B2
(45) Date of Patent: Apr. 24, 2012

(54) ANTIMICROBIALS HAVING POLYQUATERNARY AMMONIUMS AND ALCOHOL-BEARING AMIDOAMINES AND METHODS FOR THEIR USE

(75) Inventor: Zhi-Jian Yu, Irvine, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 753 days.

(21) Appl. No.: 12/055,917

(22) Filed: Mar. 26, 2008

(65) Prior Publication Data

US 2009/0247640 A1    Oct. 1, 2009

(51) Int. Cl.
*C11D 1/00*    (2006.01)
*C11D 3/30*    (2006.01)
*C11D 3/32*    (2006.01)
*C11D 3/48*    (2006.01)

(52) U.S. Cl. ........ 510/112; 510/475; 510/501; 510/504; 510/505

(58) Field of Classification Search ................. 510/112, 510/475, 501, 504, 505; 424/78.04
See application file for complete search history.

(56) References Cited

U.S. PATENT DOCUMENTS

| | | | |
|---|---|---|---|
| 4,759,595 A | | 7/1988 | Boord et al. |
| 4,777,037 A | * | 10/1988 | Wagman et al. ........... 424/70.12 |
| 5,393,491 A | * | 2/1995 | Dassanayake et al. ......... 422/28 |
| 5,631,005 A | * | 5/1997 | Dassanayake et al. .... 424/78.04 |
| 6,319,464 B1 | | 11/2001 | Asgharian |
| 6,432,420 B2 | * | 8/2002 | Ellis et al. ...................... 424/401 |
| 6,455,058 B1 | * | 9/2002 | Sun et al. ....................... 424/401 |
| 7,025,958 B2 | | 4/2006 | Schlitzer et al. |
| 7,060,260 B2 | * | 6/2006 | Fahnestock et al. ........ 424/78.03 |
| 2002/0034483 A1 | * | 3/2002 | Avery et al. ................... 424/70.1 |
| 2002/0039975 A1 | | 4/2002 | Stone et al. |
| 2003/0044373 A1 | * | 3/2003 | Avery et al. ................. 424/70.12 |
| 2007/0297992 A1 | * | 12/2007 | Schiemann et al. ............ 424/47 |

FOREIGN PATENT DOCUMENTS

WO    WO2009097028 A1    8/2009

OTHER PUBLICATIONS

International search report for application No. PCT/US2009/038107 mailed on Oct. 19, 2010, 2 pages.

\* cited by examiner

*Primary Examiner* — Gregory Delcotto
(74) *Attorney, Agent, or Firm* — Abbott Medical Optics Inc.

(57) ABSTRACT

Antimicrobial or preservative compositions with high user comfort and/or low ocular irritation. The compositions comprise a polyquaternary ammonium compound and an amidoamine having an alcohol group and exhibit synergistic antimicrobial activity. The compositions may be used as stand-alone antimicrobials/preservatives or may be incorporated into other ocular compositions such as those for ocular lens care or the treatment of ocular conditions.

6 Claims, No Drawings

ANTIMICROBIALS HAVING POLYQUATERNARY AMMONIUMS AND ALCOHOL-BEARING AMIDOAMINES AND METHODS FOR THEIR USE

BACKGROUND OF THE INVENTION

1. Field of the Invention

The present invention relates to antimicrobial ophthalmic compositions and methods for their use. The compositions may be, for example, ocular treatment compositions or ocular lens care compositions having a polyquaternary ammonium and an amidoamine having at least one alcohol group.

2. Description of Related Art

The eyes are one of the most sensitive externally-exposed organs. As a result of this sensitivity or in response to degradation, the eyes may require treatment (e.g., for dry eye or infection or corrective surgery or corrective lenses). Some of these treatments include directly applying a composition to the affected eye in order to ameliorate the condition (e.g., for dry eye or infection). For treatments requiring a lens that will directly contact the eye, a composition may be needed, for example, to store, condition, rinse, or reduce the microbial load on the lens. Most, if not all, of the compositions used for eye or lens treatment require an additive with antimicrobial, disinfective, and/or preservative capabilities. Since this antimicrobial/preservative will come into contact with the eye (either directly or via a lens), the antimicrobial/preservative should cause minimal ocular irritation or user discomfort. Many antimicrobials have been developed for ophthalmic use.

Antimicrobials for contact lens care are one type of ophthalmic antimicrobial. Contact lenses generally fall into three categories: hard lenses formed from materials prepared by polymerization of acrylic esters, such as polymethyl methacrylate (PMMA); rigid gas permeable (RGP) lenses formed from silicone acrylates and fluorosilicone methacrylates; and, soft type lenses that may be formed from traditional copolymers such as 2-hydroxyethyl methacrylate (HEMA) or from newer silicon-containing hydrogel materials. Examples of extended wear high vapor diffusion soft contact lenses include, but are not limited to, those made from silicon-containing hydrogel materials (silicone hydrogels), such as the Focus® NIGHT & DAY™ lenses from CIBA Vision (Atlanta, Ga.), and those made from Balafilcon® A, such as PUREVISION® lenses from Bausch & Lomb, Incorporated (Rochester, N.Y.).

Contact lenses typically are cleaned to remove any accumulated buildup and disinfected to kill harmful microorganisms that may be present or grow on the lenses. However, ocular tissues may be adversely impacted during contact lens wear due to exposure to preservatives, disinfecting agents, cleaning agents, and other components contained in contact lens care solutions. Exposure may occur through direct tissue contact with a solution or indirect contact with a solution that may have adsorbed or absorbed to the contact lens during cleaning/disinfection and subsequently is desorbed into the eye during contact lens wear.

Hard or rigid lenses have a lower tendency to bind ingredients used in contact lens care compositions since they possess low vapor diffusion and absorb only minor amounts of aqueous fluids. On the other hand, due to their purposely designed high rate of oxygen transmission, soft lenses have a greater tendency to bind contact lens solution ingredients. In addition, since they tend to be worn for longer periods of time, soft contact lenses also have greater opportunity to desorb any bound ingredients. These desorbed materials (e.g., antimicrobial agents) may lead to, for example, ocular irritation or discomfort. Therefore, developing lens care solutions for soft contact lenses poses particular challenges.

Many multi-purpose solutions that may be used to clean, disinfect and wet contact lenses, followed by direct insertion into the eye, are available. Multi-purpose solutions must be strong enough to kill harmful microorganisms that may be present or grow on the lenses while being gentle enough to use on the eyes. Such a solution also must be compatible with the many contact lens materials, including the silicone hydrogel materials. Measures of contact lens compatibility include contact lens discoloration, physical parameter change, fragility, and uptake/release of solution components, especially antimicrobial agents. Contact lens care solutions, such as a multi-purpose solutions (MPSs), attempt to balance cleaning and disinfection ability with safety and comfort on the eyes. The addition of more effective disinfecting agents usually has the effect of reducing contact lens material compatibility or ocular comfort of the solution. One way to achieve additional material compatibility and comfort is to reduce the amount disinfecting agent. However, conventional knowledge dictates that this results in lower antimicrobial efficacy.

The U.S. Food and Drug Administration (FDA) requires contact lens solutions to meet certain biocidal performance criteria against specified representative bacteria and fungi set in the Premarket Notification (510 k) Guidance Document For Contact Lens Care Products, Appendix B, Apr. 1, 1997 and ISO/FDIS 14729: Ophthalmic optics-Contact lens care products—Microbiological requirements and test methods for products and regimens for hygienic management of contact lenses, January 2001. These guidance documents are also known as the "stand-alone" disinfection standard. A contact lens solution that qualifies as a "Chemical Disinfecting Solution" is one that does not require rubbing to meet biocidal performance criteria known as the "Stand Alone Standard." A contact-lens solution that qualifies as a "Chemical Disinfecting System" is one that requires rubbing to pass biocidal performance criteria known as the "Regimen Standard." The FDA and ISO guidelines for both disinfection efficacy standards follow.

Stand-Alone Disinfectant (Primary) Criteria:

| Organism | Average Log Reduction at Labeled Soak Time |
| --- | --- |
| S. marcescens, ATCC 13880 | 3.0 logs |
| S. aureus, ATCC 6538 | 3.0 logs |
| P. aeruginosa, ATCC 9027 | 3.0 logs |
| C. albicans, ATCC 10231 | 1.0 log |
| F. solani, ATCC 36031 | 1.0 log |

Regimen-Dependent Disinfectant (Secondary) Criteria:

| Organism | Average Log Reduction at Labeled Soak Time |
| --- | --- |
| S. marcescens, ATCC 13880 | Minimum of 1.0 log per bacterium |
| S. aureus, ATCC 6538 | Sum of all three bacteria log-drops |
| P. aeruginosa, ATCC 9027 | Greater than or equal to 5.0 logs |
| C. albicans, ATCC 10231 | Stasis |
| F. solani, ATCC 36031 | Stasis |

For additional cleaning and comfort, some practitioners and companies recommend that rubbing be used in conjunction with a solution which is approved as a stand-alone disinfectant.

As may be deduced from the relatively lower biocidal requirements, *Candida albicans* and *Fusarium saloni* are the most antimicrobial agent resistant of the five representative bacteria and fungi. As a result, achieving adequate antimicrobial activity against *Candida* and *Fusarium* often is a difficult task when designing an antimicrobial component for a particular contact lens care solution. There is a need for an antimicrobial component that exhibits higher biocidal effect on *Candida* and *Fusarium*, even when used in relatively small amounts.

Aside from the FDA-specified representative bacteria and fungi, *Acanthamoeba* is another organism that is resistant to most antimicrobial agents. A recent increase in cyst-type *Acanthamoeba* infection among contact lens wearers in the U.S. indicates a need for an antimicrobial component that exhibits higher biocidal effect on *Acanthamoeba*. While it is known that alexidine is very biocidal against trophzoite and cyst-type *Acanthamoeba*, it is not very biocidal against *Fusarium*. There is a need for an antimicrobial component with broader biocidal efficacy.

U.S. Pat. No. 7,025,958 discloses the use of amidoamines for treating and preventing *Acanthamoeba*-related and fungal infections. The patent examples incorporate 5 ppm myristamidopropyl dimethylamine (MAPD) into Opti-Free® RepleniSH® multipurpose contact lens solution (Alcon, Inc., Fort Worth, Tex.). One disadvantage of using amidoamines in a contact lens care composition is that it has a strong tendency to adsorb onto various types of ocular lenses. As discussed above, this may lead to eye irritation after the contact lens is placed in the eye and the antimicrobial agent desorbs from the contact lens. The amidoamines disclosed in the patent also may not have a long shelf life since they may gradually migrate out of the solution to the inside wall of the plastic container. Over time, the loss of antimicrobial agent from the solution may lead to significant loss in antimicrobial efficacy.

There is need for an ophthalmic antimicrobial that exhibits broad and strong biocidal efficacy while causing minimal ocular irritation or user discomfort. The present invention addresses this need by providing an antimicrobial having two antimicrobial agents that, when combined, surprisingly have synergistic biocidal efficacy, even against more antimicrobial agent resistant microorganisms.

SUMMARY OF INVENTION

The present invention is directed to ophthalmic compositions having a synergistically-antimicrobial (or preservative) amount of a polyquaternary ammonium compound and an amidoamine comprising (having) an alcohol group. The ophthalmic compositions may be, for example, an ocular treatment composition and/or a lens care composition. The compositions may have a liquid medium, optionally an aqueous liquid medium, and an antimicrobial component. The antimicrobial component may include a synergistically-antimicrobial amount of a polyquaternary ammonium compound and an amidoamine having an alcohol group. In another embodiment, the contact lens care composition may contain from about 0.00001 to about 3% (w/w), or about 0.000075 to about 1% (w/w), of the polyquaternary ammonium compound and from about 0.00001% to about 3% (w/w), or about 0.0001% to about 1% (w/w), of the amidoamine.

In another embodiment, the amidoamine may include a tertiary alkyl amidoamine with an alcohol group, or an amidoamine with the formula R—CONCH$_2$CH$_2$CH$_2$N(CH$_3$)$_2$, where "R" is an alcohol. In another embodiment, "R" may have the formula C$_n$H$_{2n+1}$CH(OH)C$_m$H$_{2m-2}$ wherein m and n independently are integers having values of about 1 to about 18. In another embodiment, the amidoamine may include ricinoleamidopropyl dimethylamine (RAPD).

In another embodiment, the polyquaternary ammonium compound may include poly[(dimethyliminio)-2-butene-1,4-diyl chloride], α-[4-[tris(2-hydroxyethyl) ammonio]-2-butenyl]-ω-[tris(2-hydroxyethyl)ammonio]-dichloride. In another embodiment, the contact lens care composition may contain from about 0.000075 to about 1% w/w of poly[(dimethyliminio)-2-butene-1,4-diyl chloride], α-[4-[tris(2-hydroxyethyl) ammonio]-2-butenyl]-ω-[tris(2-hydroxyethyl) ammonio]-dichloride and from about 0.0001% to about 1% (w/w) of a tertiary alkyl amidoamine having the formula R—CONCH$_2$CH$_2$CH$_2$N(CH$_3$)$_2$, wherein R has the formula C$_n$H$_{2n+1}$CH(OH)C$_m$H$_{2m-2}$, wherein m and n independently are integers having values of about 1 to about 18.

In addition to the antimicrobial component, the compositions may contain any ingredients known to the artisan skilled in the ophthalmic composition arts. Some of these embodiments are exemplified hereafter. In one embodiment, the ophthalmic composition may contain a surfactant in an amount effective to, for example, act as a demulcent on an eye or clean a contact lens contacted with the composition. The surfactant may include poly(oxyethylene)-poly(oxypropylene) block copolymers, and mixtures thereof, optionally in the range of about 0.01% to about 1% (w/v). The ophthalmic composition also may contain a buffer component in an amount effective to maintain the pH of the composition within a physiologically acceptable range. The ophthalmic composition also may contain a buffer component selected from boric acid, sodium borate, and mixtures thereof in the range of about 0.01% to about 0.5% (w/v).

The ophthalmic composition also may contain a viscosity-inducing component selected from cellulosic derivatives, hyaluronic acid, hyaluronate, and mixtures thereof. The viscosity-inducing component may be present at about 0.01% to about 5% (w/v) of the total solution. The viscosity-inducing component may include hydroxypropylmethyl cellulose and hyaluronic acid at about 0.01% to about 5% (w/v) of the total solution. The ophthalmic composition also may contain a chelating component, optionally ethylenediaminetetraacetic acid, in an amount of less than 0.5% (w/v) of the total composition. The ophthalmic composition may also contain a tonicity component in an amount effective at providing the desired tonicity to the composition. The tonicity component may include about 0.1% to about 1.5% (w/v) sodium chloride.

The present invention also is directed to methods for treating an eye or an ocular lens. The methods include contacting an eye or an ocular lens with a liquid medium having an antimicrobial or preservative component that includes a synergistically-antimicrobial amount of a polyquaternary ammonium compound and an amidoamine comprising an alcohol group. The methods may utilize any of the compositions described herein, including those disclosed directly above. In addition, the contacting step may be performed for about 10 minutes or more, about 4 hours or more, or for about 6 hours or more.

DETAILED DESCRIPTION

As used herein, the term "ophthalmic" or ophthalmic composition/solution refers to anything associated with the eyes, including compositions to treat ocular conditions (e.g., dry eye or infection) and ocular lens compositions (e.g., re-wetters, disinfecting solutions, storage solutions, rinsing solutions, and multi-purpose solutions). Of course, multi-purpose contact lens care solutions are those that may be used to re-wet, disinfect, clean, store, and rinse contact lenses. The antimicrobial component of the present invention allows a user to remove a contact lens exposed to the component and place the lens in the user's eye for safe and comfortable wear; or, after the lens is exposed to the antimicrobial component (or a composition containing it), it may rinsed with another quantity of the antimicrobial component (or a composition containing it) and placed in the user's eye for safe and comfortable wear.

As used herein, the term "treating" in reference to eyes refers to ameliorating or lessening the symptoms associated with the ocular condition (e.g., dry eye or infection) or curing the ocular condition. The term "treating" in reference to lenses refers to exposing the lens to the antimicrobial component or compositions that contain it (e.g., re-wetters, disinfecting solutions, storage solutions, rinsing solutions, and multi-purpose solutions) to, for example, re-wet, disinfect, clean, store, and rinse the lenses.

As used herein, the term "ophthalmically acceptable" refers to an contact lens care solution or component thereof that is compatible with ocular tissue, i.e., it does not cause significant or undue detrimental effects when brought into contact with ocular tissue. Preferably, the antimicrobial components of the present invention also are compatible with any other components of the compositions that contain the antimicrobial components. Preferably, the antimicrobial components of the present invention and the compositions that contain them are substantially ophthalmically optimized, i.e., they minimize ocular response while delivering ophthalmic benefit(s) to the lens-wearing eye.

As used herein, the term "synergistically-effective" and "synergistically-antimicrobial" amount refers to any combined amount of polyquaternary ammonium compound and amidoamine that exhibits synergistic biocidal, antimicrobial, antibacterial, or antifungal activity against at least one microbe. As used herein, "synergistic" refers to the effect achieved with a combination of components when that effect is greater than the effect achieved with either component alone. As used herein, "synergistic" includes additive effect.

As used herein, the term "antimicrobial" refers to any agent or action that is biocidal, antimicrobial, antibacterial, or antifungal activity against any microbe. A skilled artisan will appreciate that antimicrobial as used herein also refers to a disinfectant or preservative (e.g., of an ocular solution).

As used herein, the term "ocular lens" or "lens" refers to any type of lens for implantation into or placement onto an eye.

Disclosed are ophthalmic antimicrobial components having a synergistic combination of amidoamines having at least one alcohol group and polyquaternary ammonium compounds. The antimicrobial components of the present invention provide enhanced biocidal activity over other antimicrobial agents, without significantly contributing to ocular irritation or user discomfort. In addition, the inventors surprisingly have discovered that the inventive antimicrobial components exhibit improved biocidal activity against typically antimicrobial resistant microorganisms, such as *A. polyphaga* (ATCC 30461). The present ophthalmic antimicrobial components provide a superior balance of antimicrobial activity and ophthalmic acceptability and may be used in any ophthalmic composition. Non-limiting examples of ophthalmic compositions include contact lens care compositions, re-wetting drops, treatments for eye infection, lubricating eye drops, and artificial tears.

Antimicrobial polyquaternary ammonium compounds include PHMB, Polixetonium, and polyquaternium-1. In one embodiment, the polyquaternary ammonium compound comprises polyquaternium-1, which is poly[(dimethyliminio)-2-butene-1,4-diylchloride (1:1)], a-[4-[tris(2-hydroxyethyl)ammonio]-2-buten-1-yl]-w-[tris(2-hydroxyethyl)ammonio]-chloride (chemical registry number 75345-27-6, available under the names Polyquaternium 1® from Onyx Corporation, Jersey City, N.J.; Onamer M®; Polyquad®, from Alcon Laboratories, Inc., Ft. Worth, Tex.). The polyquaternary ammonium compound preferably is present in a liquid aqueous medium at concentrations of about 0.00001%, about 0.0001% or about 0.00075%, to about 0.002%, about 0.005%, about 0.01%, about 0.1%, about 1%, or about 3% (w/w). A skilled artisan will appreciate that the polyquaternary ammonium compound may be present in a synergistically-effective amount. That is, any amount of polyquaternary ammonium compound that, when combined with a particular amount of amidoamine, exhibits synergistic biocidal activity against at least one microbe.

Amidoamines include alkylamidopropyl amine, alkylamidopropyl mono or dimethylamine, and alkylamidopropyl morpholine. Amidoamines may be purchased or synthesized in accordance with known techniques (e.g., as described in U.S. Pat. No. 5,573,726). Amidoamines include, for example, N,N-Dimethyl-N'-Tetradecanoyl-1,3-Propylenediamine (also myristamidopropyl dimethylamine phosphate, available as MIRISTOCOR® from Hoffman-La Roche Inc., Nutley, N.J. (USA); and as Schercodine® M from Scher Chemicals Inc., Clifton, N.J. (USA)); lauramidopropyl dimethylamine (available as LEXAMINE® L-13 from Inolex Chemical Company, Philadelphia, Pa. (USA)); and, stearamidopropyl dimethylamine (available as LEXAMINE® S-13 from Inolex Chemical Company). The amidoamine preferably is present in a liquid aqueous medium at concentrations of about 0.00001%, about 0.00005%, about 0.000075%, about 0.0001%, about 0.0005%, or about 0.001%, to about 0.0025%, about 0.005%, about 0.01%, about 0.1%, about 1%, or about 3% (w/w). A skilled artisan will appreciate that the amidoamine may be present in a synergistically-effective amount. That is, any amount of amidoamine that, when combined with a particular amount of a polyquaternary ammonium compound, exhibits synergistic biocidal activity against at least one microbe.

The amidoamines for use with the present invention preferably are tertiary alkyl amidoamines and/or preferably include at least one alcohol group on the molecule. A skilled artisan knows how to modify an amidoamines to bind at least one alcohol group on the molecule. Preferred tertiary alkyl amidoamines of the present invention include compounds having the formula R—CONCH$_2$CH$_2$CH$_2$N(CH$_3$)$_2$ wherein R is an alcohol, optionally an alcohol with the formula C$_n$H$_{2n+1}$CH(OH)C$_m$H$_{2m-2}$—, wherein m and n individually are integers ranging from 1 to 18, 4 to 16, or 5 to 11. Alcohol-modified tertiary alkyl amidoamines include 8-hydroxymyristoleaminopropyl dimethylamine, 7-hydroxymyristoleaminopropyl dimethylamine, 10-hydroxypamitoleaminopropyl dimethylamine, 9-hydroxypamitoleaminopropyl dimethylamine, and ricinoleamidopropyl dimethylamine. In one embodiment, the amidoamine comprises ricinoleamidopropyl dimethylamine (RAPD).

The polyquaternary ammonium compound used in the present invention may come in the form of a pure solid, a liquid concentrate, a salt, or a salt in aqueous solution. One particularly useful polyquaternary ammonium compound is polyquaternium-1 chloride in aqueous solution at a concentration of about 2 to about 50% (w/w). Likewise, the tertiary alkyl amidoamine that may be used in the present invention may come in the form of a pure liquid, a liquid concentrate, or in solution. One particularly useful form of tertiary alkyl amidoamine is a solution at a concentration of about 20 to about 40% (w/w); such solution may be aqueous.

The antimicrobial component (i.e., the combined polyquaternary ammonium compound and amidoamine) of the present invention preferably is present in a liquid aqueous medium at concentrations of about 0.00001%, about 0.0001%, or about 0.0015%, to about 0.0025%, about 0.01%, about 0.1%, about 1%, or about 3% (w/w). A skilled artisan will appreciate that the amidoamine or the polyquaternary ammonium compound may be present in any synergistically-effective amount. That is, any amount of one that, when combined with a particular amount of the other, exhibits synergistic biocidal activity against at least one microbe.

If a composition comprising the antimicrobial component is to contact the eyes (either the composition itself or via an ocular lens), it is preferred that the polyquaternary ammonium compound and amidoamine are present at ophthalmically acceptable concentrations such that ocular irritation or user discomfort are minimized or eliminated. An ophthalmic composition may comprise several ingredients and the amounts of the ingredients relative to each other may impact the ophthalmic acceptability of the composition. A skilled artisan knows how to prepare an ophthalmically acceptable composition by varying the individual amounts of ingredients.

The antimicrobial component of the present invention may be used in compositions for treating conditions of the eye. Non-limiting examples of these compositions include eye infection treatments, lubricating eye drops, and artificial tears. Aside from an antimicrobial, these compositions typically require other components. A skilled artisan is capable of preparing numerous eye treatment compositions with the present antimicrobial components. Some eye treatment compositions may include ingredients familiar to the skilled artisan including, but not limited to a drug such as cyclosporine, a lipid and oils such as polyunsaturated oils.

Compositions according to the present invention also may include a surfactant component, preferably a nonionic surfactant, in an amount effective to clean a contact lens contacted with the composition, a buffer component in an amount effective in maintaining the pH of the composition within a physiologically acceptable range if the composition directly will contact the eyes; an effective amount of a viscosity inducing component; and/or an effective amount of a tonicity component. The present compositions may also include an effective amount of a chelating or sequestering component, more preferably in a range of less than about 0.5% (w/v). The compositions of the present invention preferably are ophthalmically acceptable taking into account each of the components in the concentrations employed relative to each other. In addition, each of the components preferably is employed in amounts that permit complete solubility in the compositions.

Additional antimicrobial components may be added to the present compositions. The presently useful additional antimicrobial components include chemicals that derive their antimicrobial activity through a chemical or physiochemical interaction with microbes or microorganisms, such as those contaminating a contact lens. Suitable antimicrobial components are those generally employed in ophthalmic applications and include, but are not limited to: quaternary ammonium salts used in ophthalmic applications such as benzalkonium halides, and biguanides, such as salts of alexidine, alexidine-free base, salts of chlorhexidine, hexamethylene biguanides, and salts thereof, antimicrobial polypeptides, and the like and mixtures thereof. Cetyl pyridinium chloride (CPC) also is an antimicrobial/preservative that may be used in combination with the antimicrobial components of the present invention.

One antimicrobial commonly used in contact lens care compositions is polyhexamethylene biguanide (PHMB). When used, the concentration of PHMB may be as low as from about 0.000005 to about 0.00009 w/v % (0.05 to 0.9 ppm). Alternatively, the concentration may be from about 0.000005 to about 0.00005 w/v % (0.05 to 0.5 ppm), or from about 0.000005 to 0.000025 w/v % (0.05 to 0.25 ppm). If utilized, molecular weight fractions of PHMB may be prepared in accordance with any means known in the art including, but not limited to, molecular filtration, gel permeation chromatography (GPC), dialysis and chemical synthesis. Generally PHMB, also referred to as poly(aminopropyl biguanide) (PAPB), has molecular weights of up to about 100,000. Such compounds are known (e.g., as described in U.S. Pat. No. 4,759,595).

The present invention may be used to prepare multi-purpose compositions, that is, compositions that may be used to clean, disinfect, rinse, re-wet, and/or enhance the wearability of contact lenses. As to contact lens disinfection, it is preferred to use an amount of the antimicrobial component that reduces the microbial burden or load on the contact lens by one log order in about six hours, more preferably in about three hours, more preferably in about one hour.

If the composition of the present invention directly will contact the eyes, it is preferred that the composition have a pH in the physiologically acceptable range of about 4, about 5, or about 6 to about 8, about 9, or about 10. In particular, the solution preferably has a pH in the range of about 6 to about 8. In order to achieve or maintain the desired pH, a buffer component in an amount effective to maintain the pH may be required. The buffer component may include one or more phosphate or tromethamine (TRIS, 2-amino-2-hydroxymethyl-1,3-propanediol) buffers, for example, combinations of monobasic phosphates, dibasic phosphates, and the like, or tromethamine and tromethamine hydrochloride. Particularly useful phosphate buffers are those selected from phosphate salts of alkali and/or alkaline earth metals. Examples of suitable phosphate buffers include one or more of sodium phosphate dibasic ($Na_2HPO_4$), sodium phosphate monobasic ($NaH_2PO_4$), and the corresponding potassium phosphate salts. The buffer component also may include boric acid and/or sodium borate (e.g., sodium borate 10 hydrate). The buffer component also may include an amino acid such as taurine. Buffer components typically are used in amounts about 0.01% or about 0.02% to about 0.5% (w/v).

The present compositions may further comprise effective amounts of other components, such as a detergents or surfactants; viscosity-inducing or thickening components; chelants or sequesterants; and, tonicity agents. The additional component or components may be selected from any materials known to be useful in contact lens care compositions and may be included in amounts effective to provide the desired effect or benefit. If an additional component is included, it preferably is compatible with the other components of the composition under typical use and storage conditions. For example, the additional component or components preferably do not impact adversely the antimicrobials described herein.

A surfactant may be added to the compositions of the present invention to aid in cleaning, i.e., to at least aid in removing debris or deposit material from a contact lens contacted with the solution. Some exemplary surfactant(s) include, but are not limited to, nonionic surfactants (e.g., polysorbates like polysorbate 20, a.k.a. Tween® 20), 4-(1,1, 3,3-tetramethylbutyl) phenol/poly(oxyethylene) polymers (e.g. Tyloxapol®), poly(oxyethylene)-poly(oxypropylene) block copolymers, and combinations of these and/or other surfactants.

Nonionic surfactants are preferred for some embodiments of the present invention. Nonionic surfactants include poly (oxyethylene)-poly(oxypropylene) block copolymers, which may be obtained commercially from the BASF Corporation under the trademarks Pluronic® or Tetronic®. Pluronic® block copolymers generally can be described as polyoxyethylene/polyoxypropylene condensation polymers terminated in primary hydroxyl groups. They may be synthesized by first creating a hydrophobe of desired molecular weight by the controlled addition of propylene oxide to the two hydroxyl groups of propylene glycol or glycerin. An ethylene oxide then may be added to sandwich the hydrophobe between hydrophile groups. Tetronic® surfactants are also known as poloxamines and are symmetrical block copolymers of ethylene diamine with polyoxyethylene and polyoxypropylene.

In some embodiments of the invention, the block copolymers may have average molecular weights in the range of about 2500 to about 30,000 Daltons, more preferably about 6000 to about 18,000 Daltons. Exemplary block copolymer surfactants include: poloxamer 108, poloxamer 188, poloxamer 237, poloxamer 238, poloxamer 288 poloxamer 407, Tetronic® 904, Tetronic® 1107, Tetronic® 1304 (mol. wt. 10,500), and Tetronic® 1307. Good surfactant activity may be obtained with poloxamer 237 and Tetronic® 1304. Poloxamer 237 is also known as Pluronic F87.

The amount of surfactant component present, if any, varies over a wide range depending on a number of factors, including, the particular surfactant(s) used, any other components in the composition, and the like. Typically, the amount of surfactant may be at least about 0.005% or about 0.01% and at most about 0.1%, about 0.5%, or about 1.0% (w/v). In another embodiment, the surfactant concentration may be about 0.05% to about 0.20% (w/v).

The viscosity-inducing components employable in the present compositions preferably are those that are effective at low or reduced concentrations, are compatible with other components of the present compositions, and are nonionic. Such viscosity inducing components may act to: enhance and/or prolong the cleaning and wetting activity of any surfactant component; condition the lens surface making it more hydrophilic/less lipophilic; and/or to act as a demulcent in the eye. Increasing solution viscosity also may provide a film on the lens to facilitate comfortable wear. The viscosity-inducing component also may act to cushion the impact of contact lens insertion on the surface eye and also may serve to alleviate eye irritation.

Suitable viscosity-inducing components include, but are not limited to, water soluble natural gums, cellulose-derived polymers and the like. Natural gums include guar gum, gum tragacanth, and the like. Cellulose-derived polymers include hydroxypropyl cellulose, hydroxypropylmethyl cellulose, methyl cellulose, hydroxyethyl cellulose, and the like. Preferred viscosity-inducing agents include cellulose derivatives (polymers), and mixtures thereof. A particularly useful viscosity inducing component is hydroxypropylmethyl cellulose (HPMC).

The viscosity-inducing component is used in an amount effective to increase the viscosity of the solution, preferably to a viscosity in the range of about 1.5 to about 30 cps, or even as high as about 75 cps (measured at 25° C.), preferably as determined by USP Test Method No. 911 (USP 23, 1995). To achieve this range of viscosity increase, about 0.01% to about 5% (w/v), or about 0.05% to about 0.5% (w/v), of a viscosity-inducing component typically is employed.

In addition, it recently has been discovered that certain naturally occurring and/or synthetic anionic polymeric substances, previously presumed to be incompatible with cationic monomeric or dimeric antimicrobial agents, do not profoundly inhibit the antimicrobial activity of these cationic antimicrobial agents. These substances include carboxymethylcellulose, hyaluronic acid, hyaluronate, and mixtures thereof, and may be present in amounts ranging from about 0.001% or about 0.002%, to about 1% or about 2%. These substances have been shown to work very well with monomeric or dimeric cationic antimicrobial agents such as, for example, cetylpyridinium chloride.

A chelating or sequestering component preferably is included in an amount that enhances the efficacy of the antimicrobial component and/or complexes with any metal ions to more effectively clean the contact lens.

A wide range of organic acids, amines or compounds which include an acid group and an amine function are capable of acing as chelating components in the present compositions. For example, nitrilotriacetic acid, diethylenetriaminepentacetic acid, hydroxyethylethylene-diaminetriacetic acid, 1,2-diaminocyclohexane tetraacetic acid, hydroxyethylaminodiacetic acid, ethylenediamine-tetraacetic acid and its salts, polyphosphates, citric acid and its salts (e.g., trisodium citrate), tartaric acid and its salts, and the like and mixtures thereof, are useful as chelating components. Ethylenediaminetetraacetic acid (EDTA) and its alkali metal salts, are preferred, with disodium salt of EDTA, also known as disodium edetate, being particularly preferred.

The chelating component preferably is present in an effective amount, for example, in a range of about 0.01% and about 1% (w/v) of the solution. In a very useful embodiment, particularly when the chelating component is EDTA, salts thereof and mixtures thereof, a reduced amount is employed, for example, in the range of less than about 0.05% (w/v) or even about 0.02% (w/v) or less. Such reduced amounts of chelating component have been found to be effective in the present compositions while, at the same time, providing for reduced discomfort and/or ocular irritation.

The liquid aqueous medium used is selected to have no substantial deleterious effect on the lens being treated, or on the wearer of the treated lens. The liquid medium is constituted to permit, and even facilitate, the lens treatment or treatments by the present compositions. The liquid aqueous medium advantageously has an osmolality in the range of at least about 200-mOsmol/kg for example, about 300 or about 350, to about 400 mOsmol/kg. The liquid aqueous medium more preferably is substantially isotonic or hypotonic (for example, slightly hypotonic) and/or is ophthalmically acceptable.

The liquid aqueous medium preferably includes an effective amount of a tonicity component to provide the liquid medium with the desired tonicity. Such tonicity components may be present in the liquid aqueous medium and/or may be introduced into the liquid aqueous medium. Among the suitable tonicity adjusting components that may be employed are those conventionally used in contact lens care products, such as various inorganic salts and non-ionic polyols. Sodium chloride (NaCl) and/or potassium chloride (KCl) and the like are very useful tonicity components, as are propylene glycol, glycerin, sorbitol, mannitol and the like. The amount of tonicity component included is effective to provide the desired degree of tonicity to the solution. Such amount may be, for example, in the range of about 0.2% to about 1.5% (w/v). If a combination of sodium chloride and potassium chloride is employed, it is preferred that the weight ratio of sodium chloride to potassium chloride be in the range of about 3 to about 6 or about 8.

Methods for treating an eye or a contact lens using the antimicrobial component described herein are included within the scope of the invention. Such methods comprise contacting an eye or a contact lens with such a composition at conditions effective to provide the desired treatment to the eye or the contact lens. Contacting parameters in include, among others, temperature, pressure and time. Contacting temperature may be in the range of about 0° C. to about 100° C., more preferably in the range of about 10° C. to about 60° C., and still more preferably in the range of about 15° C. to about 30° C. Contacting at about ambient temperature is typical. The contacting may occur at about atmospheric pressure. The contacting preferably occurs for a time in the range of about 5 minutes or about 1 hour to about 2 hours, about 4 hours, about 6 hours, or about 12 hours or more. An eye to be treated may be contacted with the antimicrobial component by, for example, directly applying to the eye a liquid composition (e.g., eye drops) having the antimicrobial component. As described herein, such a composition may include other ingredients including, but not limited to, a viscosifying agent to, for example, increase the residence time of the composition in the eye or to increase user comfort.

A contact lens can be contacted with the liquid aqueous medium by immersing the lens in the medium. During at least a portion of the contacting, the liquid medium containing the contact lens can be agitated, for example, by shaking the container containing the liquid aqueous medium and contact lens, to at least facilitate removal of deposit material from the lens. After such contacting step, the contact lens may be manually rubbed to remove further deposit material from the lens. The cleaning method can also include rinsing the lens with the liquid aqueous medium or substantially free of the liquid aqueous medium prior to returning the lens to a wearer's eye. However, the method may also be as simple as contacting a lens with a solution, and placing the lens directly in an eye.

Anti-infective amidoamines previously have been described. Specifically, U.S. Pat. No. 7,025,958 discloses the use of amidoamines for treating and preventing *Acanthamoeba* and fungal infections. The disclosed amidoamines have the formula:

R—CONCH$_2$CH$_2$CH$_2$N(CH$_3$)$_2$ where R is alkyl (C$_n$H$_{2n+1}$), alkylaryl (C$_n$H$_{2n+1}$C$_6$H$_4$), or alkoxyaryl (C$_m$H$_{2m+1}$—O—C$_n$H$_{2n}$C$_6$H$_4$). One disadvantage of these amidoamines is their strong tendency to adsorb to various types of ocular lenses, such as silicone hydrogel or non-silicone hydrogel lenses, which leads to ocular irritation or user discomfort after the antimicrobial agent is released into the eye from the contact lens. Also, the disclosed amidoamines also tend to migrate out of aqueous solution towards the inside wall of plastic containers. Of course, this may lead to significant reductions in antimicrobial efficacy.

It unexpectedly was discovered that when the R group was replaced by an alcohol, particularly an alcohol with the formula C$_n$H$_{2n+1}$CH(OH)C$_m$H$_{2m-2}$, the amidoamine had significantly lower antimicrobial activity against fungi and *Acanthamoeba*. Three (3) solutions were prepared by blending together the components provided in Table 1. Approximately three (3) mL of each solution was introduced into a lens case containing a PureVision® soft contact lens. Each contact lens was maintained in this solution at room temperature for about six (6) hours. The amidoamine used was ricinoleamidopropyl dimethylamine (RAPD), an amidoamine with an alcohol group. Table 1 below provides the ingredients of the contact lens care solutions tested as well as the activity of the various solutions against *Candida* and *Fusarium* after six hours.

TABLE 1

| Ingredients | % w/w | % w/w | % w/w |
| --- | --- | --- | --- |
| RAPD | 0.0002 | 0.0005 | 0.001 |
| Propylene Glycol | 0.5 | 0.5 | 0.5 |
| Tetronic 1307 | 0.05 | 0.05 | 0.05 |
| HPMC | 0.15 | 0.15 | 0.15 |
| mono sodium-phosphate | 0.1 | 0.1 | 0.1 |
| disodium phosphate | 0.1 | 0.1 | 0.1 |
| NaCl | 0.65 | 0.65 | 0.65 |
| KCl | 0.14 | 0.14 | 0.14 |
| log drop in 6 hours in lens case with PureVision ® lens | | | |
| C. albicans | 0.26 | 0.33 | 0.21 |
| F. solani | 0.48 | 0.37 | 0.35 |

As evidenced by the antibacterial activities, a contact lens care composition comprising RAPD as the sole antimicrobial agent exhibits very low biocidal activity against *Candida* and *Fusarium*.

To test the biocidal efficacy of other solutions comprising the synergistic combination of a polyquaternary ammonium compound and an amidoamine having an alcohol group, three (3) solutions were prepared by blending together the components provided in Table 2. Approximately three (3) mL was placed into a test tube with *S. marcescens*. When utilized, the amidoamine was RAPD and the polyquaternary ammonium compound was polyquaternium-1. Table 2 below provides the ingredients of the contact lens care solutions tested as well as the activity of the solutions against *S. marcescens* after six hours.

TABLE 2

| Ingredients | % w/w | % w/w | % w/w |
| --- | --- | --- | --- |
| RAPD | | 0.002 | 0.002 |
| PQ-1 | 0.001 | 0.001 | |
| Trisodium citrate | 0.65 | 0.65 | 0.65 |
| Boric acid | 0.60 | 0.60 | 0.60 |
| Sodium borate, 10 hydrate | 0.125 | 0.125 | 0.125 |
| NaCl | 0.30 | 0.30 | 0.30 |
| EDTA | 0.05 | 0.05 | 0.05 |
| Tetronic 904 | 0.10 | 0.10 | 0.10 |
| log drop at contact time of 6 hours in test tube without lenses | | | |
| S. marcescens | 1.53 | >5.11 | 1.77 |
| log drop at contact time of 6 hours in lens case with PureVision lens | | | |
| S. marcescens | 1.07 | 3.19 | 0.91 |

As evidenced by the antibacterial activities, a contact lens care composition comprising the synergistic combination of an amidoamine having an alcohol group and polyquaternium-1 exhibits far better biocidal activity against *C. albicans* and *S. marcescens* after six hours compared to solutions having only one of these antimicrobials. In fact, the synergistic effect provided more than one log drop of additional antimicrobial efficacy.

Further testing was performed to test the biocidal efficacy of other solutions comprising the synergistic combination of a polyquaternary ammonium compound and an amidoamine having an alcohol group. In this test, five (5) solutions were prepared by blending together the components provided in Table 3. Approximately three (3) mL was placed into a test tube with S. marcescens. When utilized, the amidoamine was RAPD and the polyquaternary ammonium compound was polyquaternium-1. Table 3 below provides the ingredients of the contact lens care solutions tested as well as the activity of the solutions against S. marcescens after six hours.

TABLE 3

| Ingredients | % w/w | % w/w | % w/w | % w/w | % w/w |
|---|---|---|---|---|---|
| RAPD | | 0.0005 | 0.0005 | 0.001 | 0.001 |
| PQ-1 | 0.001 | 0.001 | | 0.001 | |
| Trisodium citrate | 0.65 | 0.65 | 0.65 | 0.65 | 0.65 |
| Boric acid | 0.60 | 0.60 | 0.60 | 0.60 | 0.60 |
| Sodium borate, 10 hydrate | 0.125 | 0.125 | 0.125 | 0.125 | 0.125 |
| NaCl | 0.30 | 0.30 | 0.30 | 0.30 | 0.30 |
| EDTA | 0.05 | 0.05 | 0.05 | 0.05 | 0.05 |
| Tetronic 904 | 0.10 | 0.10 | 0.10 | 0.10 | 0.10 |
| log drop at contact time of 6 hours in test tube without lenses | | | | | |
| S. marcescens | 1.53 | 2.51 | 0.44 | 4.2 | 1.51 |

As evidenced by the antibacterial activities, a contact lens care composition comprising the synergistic combination of an amidoamine having an alcohol group and polyquaternium-1 exhibits far better biocidal activity against S. marcescens after six hours compared to solutions having only one of these antimicrobials.

To test the biocidal efficacy of a solution comprising the synergistic combination of a polyquaternary ammonium compound and an amidoamine having an alcohol group, four (4) solutions were prepared by blending together the components provided in Table 4. Approximately three (3) mL of three of the solutions was placed into a test tube with A. polyphaga. When utilized, the amidoamine was RAPD and the polyquaternary ammonium compound was polyquaternium-1. Table 4 below provides the ingredients of the contact lens care solutions tested as well as the activity of the solutions against Acanthamoeba polyphaga after six hours.

TABLE 4

| Ingredients | % w/w | % w/w | % w/w | % w/w |
|---|---|---|---|---|
| CPC | 0.00013 | | 0.00013 | 0.00013 |
| PQ-1 | 0.001 | | 0.001 | 0.001 |
| RAPD | | 0.0005 | 0.0010 | 0.0005 |
| Trisodium citrate | 1.00 | 1.00 | 1.00 | 1.00 |
| Boric acid | 0.60 | 0.60 | 0.60 | 0.60 |
| Sodium borate, 10 hydrate | 0.125 | 0.125 | 0.125 | 0.125 |
| NaCl | 0.20 | 0.20 | 0.20 | 0.20 |
| EDTA | 0.02 | 0.02 | 0.02 | 0.02 |
| Tetronic 904 | 0.040 | 0.040 | 0.040 | 0.040 |
| Pluronic F87 | 0.05 | 0.05 | 0.05 | 0.05 |
| log drop in 6 hours in lens case with PureVision lens | | | | |
| C. albicans | 0.44 | <0.28 | 1.16 | 0.41 |
| log drop in 6 hours in test tube | | | | |
| Acanthamoeba polyphaga | 0.3 | 0.18 | 1.46 | 1.18 |

As evidenced by the antibacterial activities, contact lens care compositions comprising the synergistic combination of RAPD and polyquaternium-1 exhibit excellent biocidal activity against various representative microbes and A. polyphaga.

To test the biocidal efficacy of other solutions comprising the synergistic combination of a polyquaternary ammonium compound and an amidoamine having an alcohol group, three (3) solutions were prepared by blending together the components provided in Table 5. Approximately three (3) mL of two of the solutions was placed into a test tube with A. polyphaga. When utilized, the amidoamine was RAPD and the polyquaternary ammonium compound was polyquaternium-1. Table 5 below provides the ingredients of the contact lens care solutions tested as well as the activity of the solutions against A. polyphaga after six hours.

TABLE 5

| Ingredients | % w/w | % w/w | % w/w |
|---|---|---|---|
| PQ-1 | 0.001 | 0.001 | |
| RAPD | | 0.002 | 0.002 |
| CPC | 0.00013 | 0.00013 | |
| Trisodium citrate | 1 | 1 | 1 |
| Boric acid | 0.9 | 0.9 | 0.9 |
| Sodium borate, 10 hydrate | 0.19 | 0.19 | 0.19 |
| NaCl | 0.1 | 0.1 | 0.1 |
| EDTA | 0.02 | 0.02 | 0.02 |
| Pluronic P103 | 0.04 | 0.04 | 0.04 |
| Pluronic F87 | 0.04 | 0.04 | 0.04 |
| PEG400 | 0.3 | 0.3 | 0.3 |
| HPMC | 0.1 | 0.1 | 0.1 |
| Hyaluronic acid | 0.01 | 0.01 | 0.01 |
| log drop in 6 hours in test tube | | | |
| A. polyphaga | 0.39 | >3.0 | 1.90 |

As evidenced by the antibacterial activities, a contact lens care composition comprising the synergistic combination of RAPD and polyquaternium-1 exhibits far better biocidal activity against C albicans and A. polyphaga after six hours compared to solutions having only one of these antimicrobials.

In addition to the low biocidal effects of the alcohol-modified amidoamines (e.g., those with formula $C_nH_{2n+1}CH(OH)C_mH_{2m-2}CONCH_2CH_2CH_2N(CH_3)_2$), it appears that contact lens and plastic container wall uptake also is very low. Without wishing to be bound by theory, it is believed that the weak antimicrobial activities and low contact lens and plastic container wall uptake are due to these compounds' unique balance of molecular hydrophobicity and hydrophilicity. At physiological pHs, the tertiary amine, $-N(CH_3)_2$, will convert into a quaternary amine, $-N^+H(CH_3)_2$. Since $-OH$ and cationic $-N^+H(CH_3)_2$ are hydrophilic, the amidoamine molecule generally will be "N" shaped in aqueous solutions.

Without wishing to be bound by theory, it is believed that quaternary molecules such as those disclosed in U.S. Pat. No. 7,025,958 are "I" shaped with one hydrophilic group and one hydrophobic chain arranged at opposite sides of the molecule. In other words, the molecular conformations are hydrophobic-hydrophilic. It is believed this molecular structure allows the hydrophobic group thereon to penetrate deep into the microbe's wall, plastic container, and contact lens material, which explains the high antimicrobial activity, heavy loss to the container wall during storage, and high toxicity to the eyes (e.g., when released from the lens).

Without wishing to be bound by theory, it is believed that amidoamines of the present invention (e.g., those with formula $C_nH_{2n+1}CH(OH)C_mH_{2m-2}CONCH_2CH_2CH_2N(CH_3)_2$), however, have unique molecular conformations of hydrophobic-hydrophilic-hydrophobic-hydrophilic. It is believed the strong double hydrophilic heads and the three bulky but relatively weak hydrophobic chains make it more difficult for the molecule to penetrate the plastic container wall and contact lens material, which makes these molecules ideal antibacterial agents. However, it is believed this very molecular conformance also reduces the molecules' ability to penetrate the microbial wall resulting in low antimicrobial activity. The addition of the alcohol group, while providing certain advantages, also made the amidoamines almost useless as antimicrobial agents. However, the alcohol-modified amidoamines' advantages were realizable again when it surprisingly was discovered that they have strong antimicrobial synergism when mixed with quaternary ammonium compounds, which boosts the modified amidoamines' biocidal activity.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a" and "an" and "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus providing written support for all Markush groups used in the appended claims.

Certain embodiments of this invention are described herein. Of course, variations of these embodiments will become apparent to those of ordinary skill in the art upon reading the preceding description and the appended claims. The inventors expect skilled artisans to employ such variations as appropriate and the inventors intend for the invention to be practiced otherwise than specifically described. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, references have been made to patents and printed publications throughout this specification. Each of the above cited references and printed publications are herein individually incorporated by reference in their entirety.

It should be understood that the disclosed embodiments of the invention are for illustrative purposes only. A skilled artisan, upon reading the specification and claims, will be capable of devising other embodiments that fall within the scope of the appended claims. Accordingly, the present invention is not limited to that which is specifically shown and described.

What is claimed is:

1. An ophthalmic composition consisting of:
water, a surfactant, a buffer, a tonicity component, a chelating component and an antimicrobial component, wherein said antimicrobial component is a synergistically-antimicrobial amount of poly[(dimethyliminio)-2-butene-1,4-diylchloride (1:1)], a-[4-[tris(2-hydroxyethyl)ammonio]-2-buten-1-yl]-w-[tris(2-hydroxyethyl)ammonio]-chloride and an amidoamine having an alcohol group, the amidoamine having the formula R—$CONCH_2CH_2CH_2N(CH_3)_2$ where R is said alcohol.

2. An ophthalmic composition according to claim 1, wherein said poly[(dimethyliminio)-2-butene-1,4-diylchloride (1:1)], a-[4-[tris(2-hydroxyethyl)ammonio]-2-buten-1-yl]-w-[tris(2-hydroxyethyl)ammonio]-chloride is present in an amount from about 0.00001% to about 3% w/w and said amidoamine having an alcohol group is present in an amount from about 0.00001% to about 3% w/w.

3. An ophthalmic composition according to claim 1, wherein said poly[(dimethyliminio)-2-butene-1,4-diylchloride (1:1)], a-[4-[tris(2-hydroxyethyl)ammonio]-2-buten-1-yl]-w-[tris(2-hydroxyethyl)ammonio]-chloride is present in an amount from about 0.00075 to about 1% w/w and said amidoamine having an alcohol group is present in an amount from about 0.0001% to about 1% w/w.

4. An ophthalmic composition according to claim 1, wherein R has the formula $C_nH_{2n+1}CH(OH)C_mH_{2m-2}$, wherein m and n independently are integers having values of about 1 to about 18.

5. An ophthalmic composition according to claim 1, wherein said amidoamine is ricinoleamidopropyl dimethylamine.

6. An ophthalmic composition according to claim 1, having from about 0.00075 to about 1% w/w of poly[(dimethyliminio)-2-butene-1,4-diylchloride (1:1)], a-[4-[tris(2-hydroxyethyl)ammonio]-2-buten-1-yl]-w-[tris(2-hydroxyethyl)ammonio]-chloride and from about 0.0001% to about 1% w/w of said amidoamine wherein R has the formula $C_nH_{2n+1}CH(OH)C_mH_{2m-2}$, wherein m and n independently are integers having values of about 1 to about 18.

* * * * *